United States Patent
Marshall et al.

(10) Patent No.: US 8,652,158 B2
(45) Date of Patent: *Feb. 18, 2014

(54) LANCETS

(75) Inventors: Jeremy Marshall, Oxford (GB); Mark Eaton, Oxon (GB)

(73) Assignee: Owen Mumford Limited, Oxfordshire (GB)

( * ) Notice: Subject to any disclaimer, the term of this patent is extended or adjusted under 35 U.S.C. 154(b) by 130 days.

This patent is subject to a terminal disclaimer.

(21) Appl. No.: 12/724,628

(22) Filed: Mar. 16, 2010

(65) Prior Publication Data

US 2010/0174305 A1     Jul. 8, 2010

Related U.S. Application Data

(62) Division of application No. 10/567,554, filed as application No. PCT/GB2004/003676 on Aug. 27, 2004, now Pat. No. 7,713,280.

(30) Foreign Application Priority Data

Aug. 29, 2003   (GB) .................................. 0320283.5

(51) Int. Cl.
    *A61B 5/151*         (2006.01)
(52) U.S. Cl.
    USPC ........................................................ 606/181
(58) Field of Classification Search
    USPC ............................ 606/167, 181–183; 600/583
    See application file for complete search history.

(56) References Cited

U.S. PATENT DOCUMENTS

| | | | |
|---|---|---|---|
| 3,375,381 A * | 3/1968 | Tavel | 310/81 |
| 4,203,446 A | 5/1980 | Hofert et al. | |
| 4,527,561 A * | 7/1985 | Burns | 606/182 |
| 4,616,649 A | 10/1986 | Burns | |
| 4,860,740 A | 8/1989 | Kirk et al. | |
| 4,869,249 A * | 9/1989 | Crossman et al. | 606/182 |
| 5,324,302 A | 6/1994 | Crouse | |
| 5,746,761 A * | 5/1998 | Turchin | 606/181 |
| 5,908,434 A * | 6/1999 | Schraga | 606/181 |
| 5,954,738 A | 9/1999 | LeVaughn et al. | |
| 6,053,930 A | 4/2000 | Ruppert | |
| 6,152,935 A | 11/2000 | Kammerer et al. | |
| 6,168,606 B1 * | 1/2001 | Levin et al. | 606/181 |
| 6,299,626 B1 | 10/2001 | Viranyi | |
| 6,540,763 B2 | 4/2003 | Teo et al. | |
| 6,616,616 B2 * | 9/2003 | Fritz et al. | 600/583 |

(Continued)

FOREIGN PATENT DOCUMENTS

| | | |
|---|---|---|
| JP | 61079450 | 4/1986 |
| JP | 10192262 | 7/1998 |
| JP | 2002-143132 | 5/2002 |

*Primary Examiner* — Kathleen Holwerda
(74) *Attorney, Agent, or Firm* — Young & Thompson

(57) ABSTRACT

A return spring arrangement for a lancet (6) is provided by a pair of undulating plastic webs (14) formed integrally with the lancet. The undulations of the two webs (14) are shown out of phase with one another. These webs (14) are flexible and thus are caused to concertina when the tips (15) of the webs hit the interior of a lancet holder on release of a drive spring. The energy stored within the collapsed webs (14) is then released to drive the lancet back within the lancet holder. This positive return of the lancet ensures that a needle (5) will retract safely into the lancet holder, after operation, and does not rely on the spring being locked into the lancet holder and onto the lancet.

9 Claims, 2 Drawing Sheets

(56) References Cited

U.S. PATENT DOCUMENTS

| | | | |
|---|---|---|---|
| 7,713,280 B2 * | 5/2010 | Marshall et al. | 606/181 |
| 2002/0087180 A1 | 7/2002 | Cunningham | |
| 2002/0120216 A1 * | 8/2002 | Fritz et al. | 600/583 |
| 2004/0127818 A1 * | 7/2004 | Roe et al. | 600/583 |
| 2007/0016239 A1 * | 1/2007 | Sato et al. | 606/181 |
| 2007/0135828 A1 | 6/2007 | Rutynowski | |

* cited by examiner

LANCETS

CROSS REFERENCE TO RELATED APPLICATIONS

This application is a division of application Ser. No. 10/567,554 (now U.S. Pat. No. 7,713,280) filed on Mar. 15, 2006, which is the 35 U.S.C. §371 national stage of International PCT/GB04/03676 filed on Aug. 27, 2004, which claims priority to British Application No. 0320283.5 filed on Aug. 29, 2003. The entire contents of each of the above-identified applications are hereby incorporated by reference. Any disclaimer that may have occurred during prosecution of the above referenced applications is hereby expressly disclaimed.

BACKGROUND OF THE INVENTION

Lancet devices are used for taking blood samples by projecting a needle rapidly and momentarily out of the casing so as to prick the skin of a patient. The device needs to have some means of causing the needle to be returned into the casing after it has served its purpose and there is usually a drive spring which, when released, drives the needle forwards, overshooting its static position. It then returns to this position to drive the needle back in the casing. It is an object of this invention to provide spring return means for the lancet which is relatively cheap to manufacture and simple to install, and which removes the need for locating the return spring at the casing and lancet.

SUMMARY OF THE INVENTION

According to the invention there is provided a lancet comprising a body having a drive head at one end and a projecting needle at the other end, the body having integral webs projecting down both sides towards the location of the tip of the projecting needle, the webs being of undulating form and of a flexible material so as to act as spring members.

By utilising undulating webs as spring members, the webs can be moulded at the same time as the body of the lancet, thus saving on both manufacturing and assembly time as there is no separate return spring device which needs to be attached.

The undulations of the two webs may be out of phase with one another.

The lancet is ideally provided with a removable protective cap which is situated over the exposed end of the needle. The cap could be linked to the free ends of the webs by breakable connecting parts.

The invention also extends to a lancet holder comprising a casing housing a lancet of this invention as hereinbefore defined, and having a drive spring positioned between an end of the housing and the drive head of the lancet.

A release structure for the lancet can be provided in the form of the drive head of the lancet incorporating a flange resting against a moveable rib of the casing, together with a flexible button on the casing which is movable to release the rib from the flange to enable the drive spring to drive the lancet forwards.

The needle tip can be covered by a removable protective cap provided with a head which locates over flanges on the casing, but can be twisted out of contact with the flanges to enable the cap to be removed to expose the tip of the needle.

BRIEF DESCRIPTION OF THE DRAWINGS

The invention may be performed in various ways and a preferred example thereof will now be described, with reference to the accompanying diagrammatic drawings, in which.

DETAILED DESCRIPTION OF THE INVENTION

Figure 1:
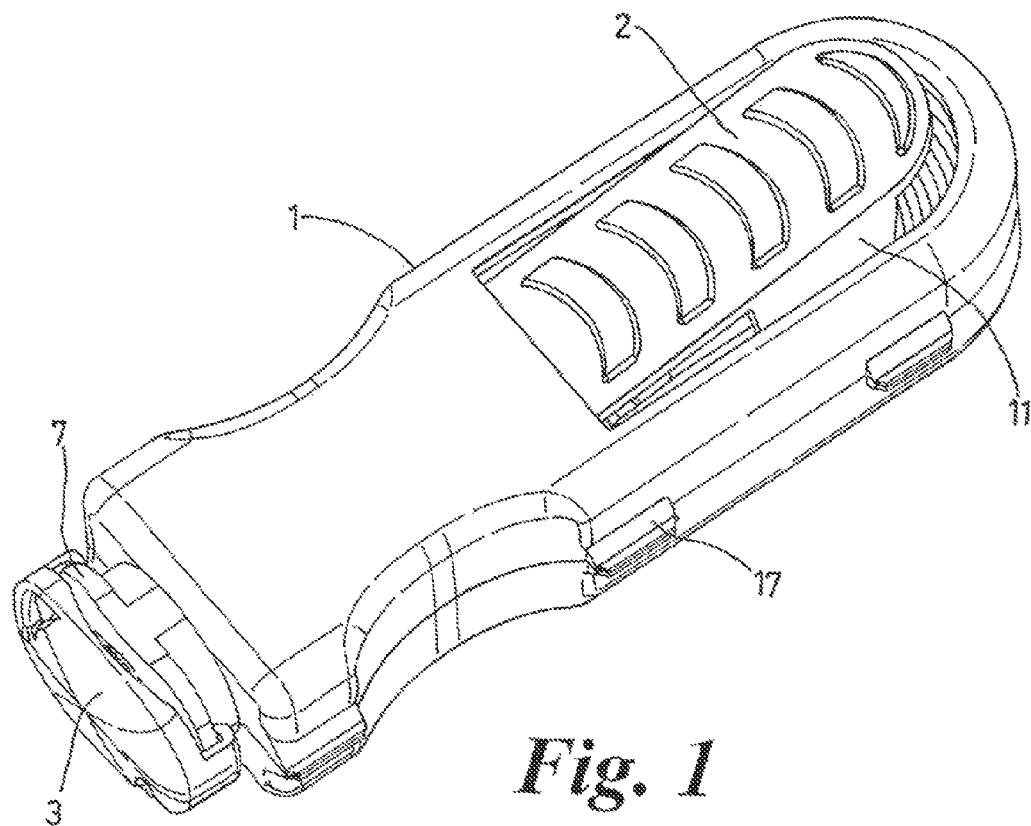
FIG. 1 is a perspective view of a lancet holder of this invention.
Figure 3:
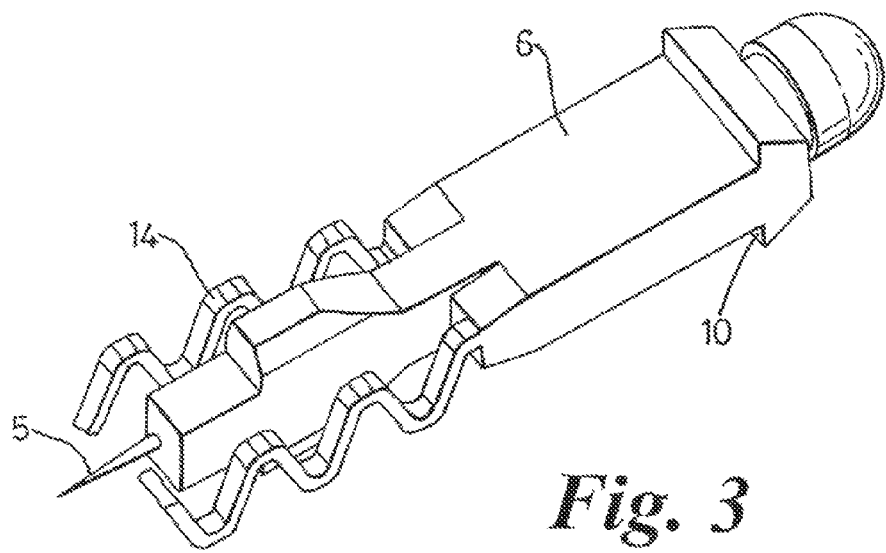
FIG. 3 is an illustration of a lancet as is enclosed within the holder of FIGS. 1 and 2.
Figure 2:
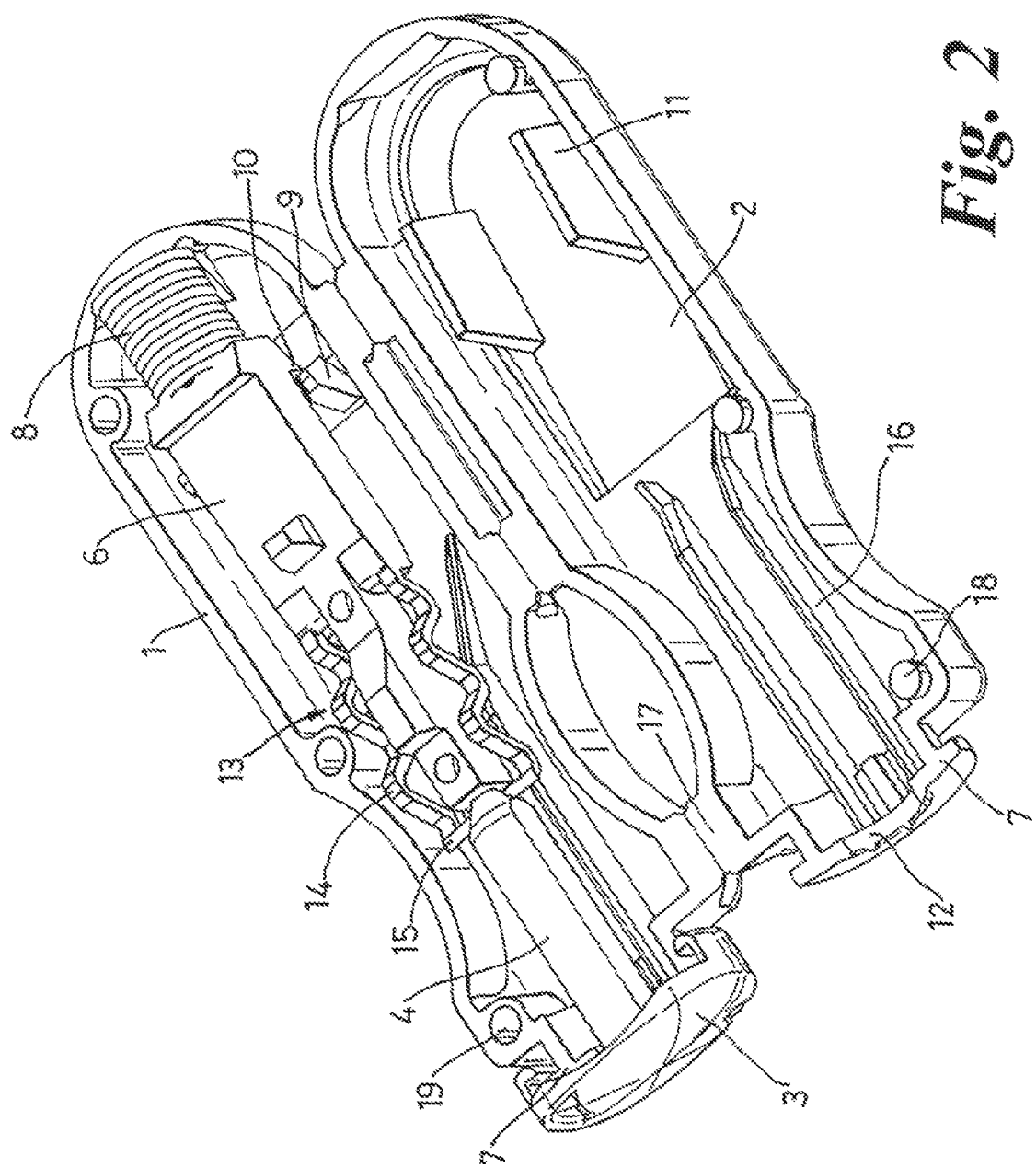
FIG. 2 illustrates the lancet holder of FIG. 1 in an opened condition.

The lancet holder shown in FIG. 1 comprises an outer casing 1 from which projects an operating button 2. At the other end, the head 3 of a protective cap projects. As can be seen from FIG. 2, the cap has an extending shaft 4 which covers and protects the tip of a needle 5 of a lancet 6 (see FIG. 3). The head 3 of the cap can be twisted to release it from engagement with flanges 7 at the end of the casing 1, enabling the cap to be pulled free of the needle 5 on the end of the lancet 6, when the device is to be used.

The lancet 6 is primed by a spring 8, but is held within the casing 1 by a rib 9 forming part of the casing 1 resting against a flange 10 on the lancet 6. In use, webs 11 on the operating button 2 will move further inwardly of the casing 1 when the button 2 is pressed, and will move the rib 9 (which is resiliently attached to the casing 1) away from the flange 10, thus releasing the lancet 6. The lancet is now driven forwardly by the coil spring 8 to cause the needle 5 to project through an opening 12 in the end of the casing 1. With the casing 1 held against the skin of a patient (prior to operation of the button 2), the needle will then penetrate the skin to enable a small blood sample to be taken.

As is usual with such lancets the needle only projects momentarily and then is withdrawn automatically into the housing 1. This is usually partly by a bounce-back of the spring 8. However, for this device a spring arrangement 13 positively pushes the lancet back into the casing. This spring arrangement is created by a pair of undulating plastic webs 14 formed integrally with the lancet 6. These webs 14 are flexible and thus are caused to concertina when the tips 15 of the webs hit the interior of the flange members 7. The energy stored within the collapsed webs 14 is then released to drive the lancet back within the casing 1. As can be seen from FIG. 3, the undulations of the two webs 14 may be out of phase with one another. This positive return of the lancet ensures that the needle will retract safely into the casing, and does not rely on the spring being locked into the casing and onto the lancet.

During manufacture the lancet body 6 is moulded about the needle 5 and the webs 14 are moulded integrally with the body 6. The tips 15 of the webs 14 can additionally be linked, during the moulding process, by thin connecting parts to the shaft 4 of the cap for the needle. This holds the cap against being twisted accidentally. However, when a deliberate twisting motion is created on the head 3 of the cap, the thin connecting parts linked to the webs 14 fracture, thus allowing the cap to be removed. As can be seen particularly from FIG. 2, guide ribs 16 are formed within both halves of the casing 1 to guide the lancet whilst it is being driven by the spring 8. The two halves of the casing 1 are integrally moulded to incorporate flexible hinges 17. When the lancet 6 and cap 3, together with the spring 8, have been loaded into one half of the casing, the two halves of the casing can be folded together so that studs 18 enter tight fitting holes 19 to grip the two halves of the casing together.

What is claimed is:

1. A lancet holder including a casing housing a lancet, the lancet comprising:

a body having a drive head at one end and a projecting needle at an other end, the body having two webs molded integrally with said body and projecting along respective sides of said body towards a tip of the projecting needle, each of the webs having one end merging with the body and another end spaced from the body and each of the webs being of undulating form when in a relaxed condition and of a flexible material so as to act as spring members to return the lancet to a retracted position;

the lancet holder having a drive spring positioned between an end of the casing and the drive head of the lancet.

2. The lancet holder according to claim 1, wherein the undulations of the two webs are out of phase with one another.

3. The lancet holder according to claim 2, wherein a removable protective cap is provided over an exposed end of the needle.

4. The lancet holder according to claim 1, wherein a removable protective cap is provided over an exposed end of the needle.

5. The lancet holder according to claim 4, wherein the cap is linked to free ends of the two webs by breakable connecting parts.

6. The lancet holder according to claim 1, wherein the drive head of the lancet incorporates a flange resting against a movable rib of the casing and a flexible button on the casing is moveable to release the rib from the flange to enable the drive spring to drive the lancet forwards.

7. The lancet holder according to claim 6, wherein the needle tip is covered by a removable protective cap provided with a head which locates over flanges on the casing, but can be twisted out of contact with the flanges to enable the cap to be removed to expose the tip of the needle.

8. The lancet holder according to claim 1, wherein the needle tip is covered by a removable protective cap provided with a head which locates over flanges on the casing, but can be twisted out of contact with the flanges to enable the cap to be removed to expose the tip of the needle.

9. The lancet holder according to claim 1, wherein said body includes a substantially planar portion adjacent to said one end having the drive head, a plane passing through each undulation of a respective one of said webs being perpendicular to said planar portion.

* * * * *